United States Patent [19]

Bushman

[11] Patent Number: 5,345,308
[45] Date of Patent: * Sep. 6, 1994

[54] OBJECT DISCRIMINATOR

[75] Inventor: Boyd B. Bushman, Lewisville, Tex.

[73] Assignee: Lockheed Corporation, Fort Worth, Tex.

[ * ] Notice: The portion of the term of this patent subsequent to Nov. 23, 2010 has been disclaimed.

[21] Appl. No.: 947,281

[22] Filed: Sep. 17, 1992

Related U.S. Application Data

[63] Continuation-in-part of Ser. No. 851,281, Feb. 7, 1992, Pat. No. 5,264,916.

[51] Int. Cl.$^5$ .............................................. G01J 4/00
[52] U.S. Cl. ..................... 356/364; 359/371; 359/407; 359/501; 250/330; 250/342
[58] Field of Search ............... 356/364, 366, 367, 368; 359/371, 386, 407, 483, 485, 501; 250/330, 342

[56] References Cited

U.S. PATENT DOCUMENTS

| | | | |
|---|---|---|---|
| 3,549,259 | 12/1967 | Klatchko. | |
| 4,202,601 | 5/1980 | Burbo et al. | 350/159 |
| 4,601,552 | 7/1986 | Jessmore | 350/551 |
| 5,138,162 | 8/1992 | Hacskaylo | 250/330 |
| 5,264,916 | 11/1993 | Bushman | 356/364 |

Primary Examiner—Mark Hellner
Attorney, Agent, or Firm—James E. Bradley

[57] ABSTRACT

A device will detect man-made objects by using a polarizer mounted to a video camera. The polarizer rotates about an axis in front of a lens array of the video camera. The rotation of the polarizer alternately polarizes light received in proportion to the speed of rotation. This produces flashing in intensity for detecting the object as well as background rejection due to its lack of polarization. A man-made object having both horizontal and vertical surfaces of a type that will reflect light that can be polarized will provide flashing through the lens array as the polarizer passes through horizontal and vertical position. On the other hand, backgrounds don't have polarized components and won't flash. Attention is drawn to the man-made target. A high pass filter between the video signal processor and the monitor reduces background from the observed scene, permitting precise lock-on to the target.

17 Claims, 4 Drawing Sheets

OBJECT DISCRIMINATOR

CROSS REFERENCE TO RELATED APPLICATION

This application is a continuation-in-part of application Ser. No. 07/851,281, filed Feb. 7, 1992, now U.S. Pat. No. 5,264,916, Object Detection System, Boyd B. Bushman.

BACKGROUND OF INVENTION

1. Field of Invention

This invention relates in general to detecting objects by detecting light reflections from an object, and in particular to a system that utilizes a polarizer for viewing the differences between vertical and horizontal polarization of the light reflected from an object.

2. Description of the Prior Art

This invention deals with a method of detecting objects, such as military targets. The targets may be trucks, tanks, artillery, aircraft, command centers and other systems. These objects may be protected by camouflage, foliage, or may be painted with a camouflage paint.

Presently, objects are detected visually through binoculars. Objects also may be detected by other techniques such as radar, infrared and night vision amplification systems. The prior systems do not always adequately detect an object, particularly objects that are camouflaged.

There are needs for detecting objects other than in military applications also. For example, the highest reason for helicopter crashes is due to collisions with high-tension electric wires, guy wires or other suspended cables. These cables are difficult to see by the pilot. At present, there is no particular means for detecting such cables other than visually.

SUMMARY OF THE INVENTION

In this invention, a light ray polarizer is employed for detecting objects. The polarizer is of a conventional type, having a large number of very finely spaced parallel lines or a polarizing filter. Military vehicles have high concentrations of non-conductors of electricity, such as glass, plastic, paints, rubbers, etc. Non-conductors have a high light contrast or modulation when seen by a polarizer that is rotated. The polarizer observes this polarized light effect only when it is sequentially oriented in certain rotational positions. The polarized reflected light from these objects is extremely different in intensity from light reflected from these objects that is not polarized. Consequently, rotating a light polarizer in front of a lens system will cause a manmade object, such as a military vehicle, to flash as the polarizer rotates between the polarizing positions. The contrast is even more pronounced on overcast days.

Natural backgrounds do not show the polarizing contrast because of their textures and/or electrical conductivities. Military vehicles normally have smoother surfaces and a lower electrical conductivity. Consequently, as the polarizer is rotating, the background surrounding the military vehicle gives a steady signal which is not highlighted to the eye. The fluctuating targets stand out, giving away their location. Neither camouflage nor moderate foliage stops the systems from highlighting military targets because adequate flashing still can be observed. This system is also applicable to detecting high-tension electrical wires.

In one embodiment, the polarizer is mounted in the image path of a video camera. A motor and gear drive gear teeth mounted to the perimeter of the polarizer. The observer will see flashes of smooth man-made objects as the polarizer rotates while the background remains uniform. The flashes pinpoint military targets to an observer.

The video camera is conventional, having a scanning device which provides signals to a video processor. The video processor provides electrical signals to a monitor or display. In this invention, a high pass filter locates between the signal processor and the display. The high pass filter can be varied to pass only signals above a selected frequency. The cut-on frequency may be selected to be in the range from 100 KHZ to two MHZ. The high pass filter reduces the background viewed by the monitor.

Also, the system may have features to distinguish if the object being detected has both horizontal and vertical surfaces to distinguish sky and water from man-made objects. A natural horizontal surface such as a lake will reflect light which will polarize. Consequently, flashes would appear as the polarizer rotates. Similarly, on clear days, the light from certain parts of the sky will polarize, also providing flashes proportionate to the speed of rotation. Water surfaces reflect the sky condition. Man-made targets will have both generally horizontal and vertical surfaces, unlike the sky or a body of water. Consequently, a rotating polarizer will flash each time the lines are horizontal and each time the lights are vertical. On the other hand, if the lens is pointed toward a body of water, the flash would occur only after the lens is moved out of its horizontal orientation. Consequently, only one-half of the flashes would be observed, and the man-made target can be distinguished from this background.

An electronic circuit will time the speed and rotational position of the polarizer and determine if flashing is occurring both when the polarizer is oriented horizontally and when oriented vertically. A mixing circuit will add the signals only if both a horizontal and a vertical component for the object is detected. This indicates a three-dimensional man-made object has been observed.

The system sees no difference for natural items such as dirt, trees, mountains and most skies. The system eliminates these images from the screen and displays only the man-made targets. This background elimination is important for reconnaissance.

DETAILED DESCRIPTION OF INVENTION

Figure 1:
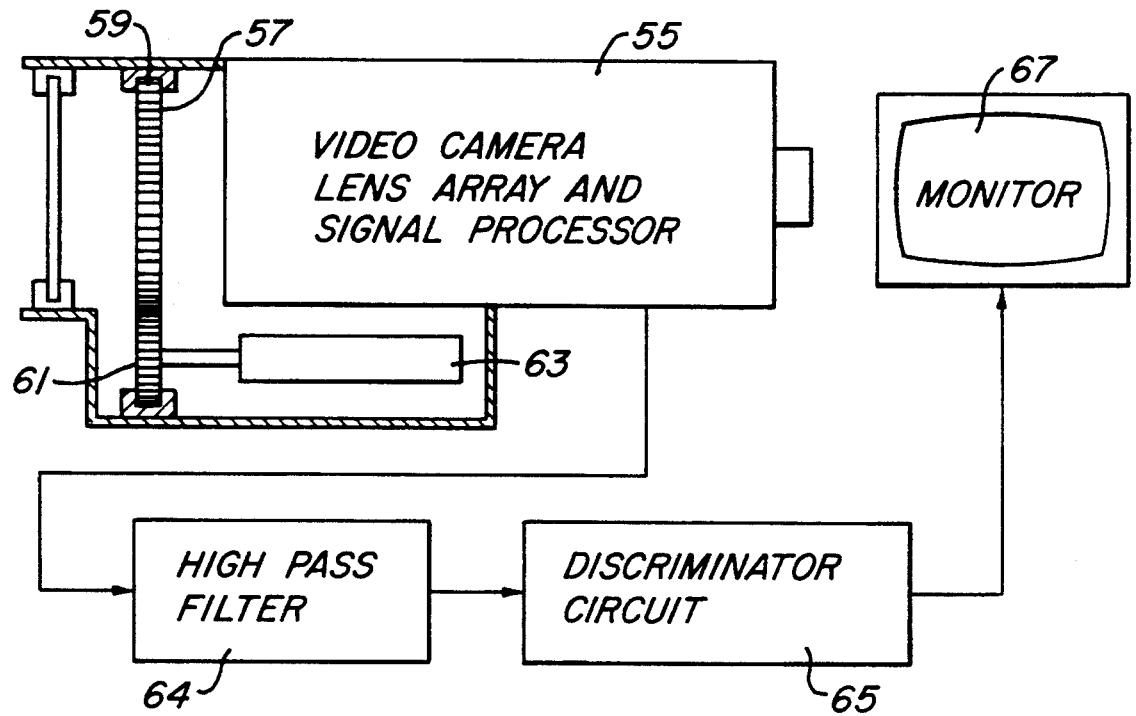
FIG. 1 is a schematic view of a video camera having a rotating polarizer mounted to it and block diagrams illustrating circuitry in accordance with this invention.
Figure 2:
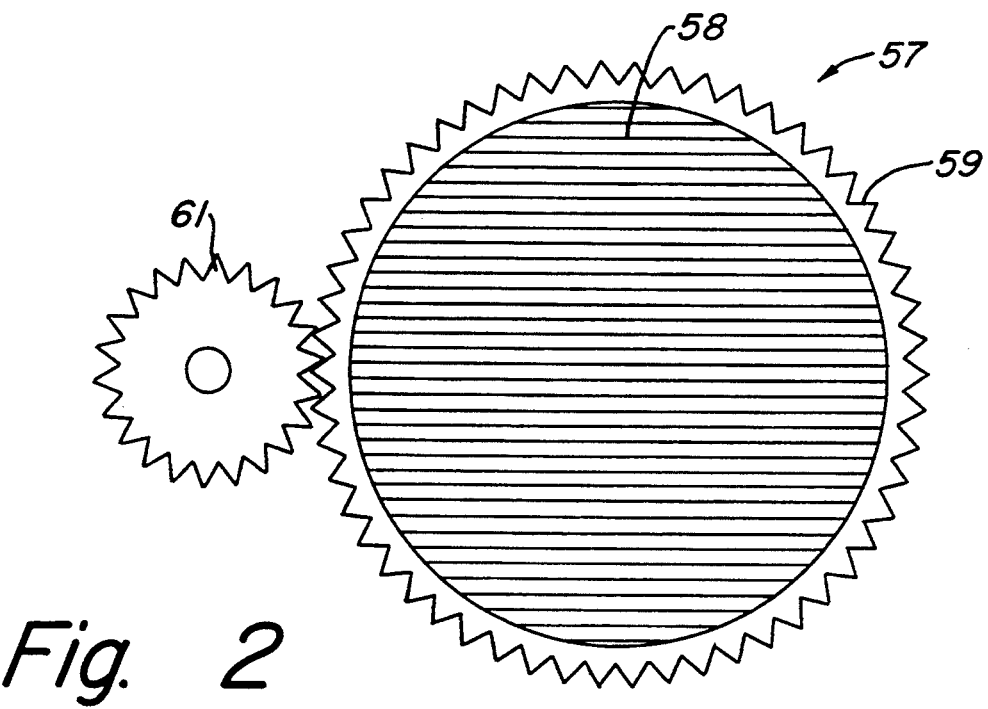
FIG. 2 is an enlarged, schematic, front view of the polarizer of FIG. 1.

Referring to FIG. 1, a video camera 55 is shown having a polarizer 57 mounted in front of its image path. Polarizer 57 is a conventional commercially available polarizer. As shown in FIG. 2, polarizer 57 has a large number of lines 58 formed thereon, which may be scribed or otherwise etched on the surface. Also, the polarizer 57 may be formed by a chemical coating which aligns the molecules in parallel lines. Polarizer cubes are also commercially available. Lines 58 are extremely closely spaced and are parallel to each other. FIG. 2 exaggerates the distance between lines 58, as the distance would not be visible to the naked eye. The distance between lines 58 is less than the wavelength of light for which the polarizer is designed.

Polarizers such as polarizer 57 have been known in the past. It is known that they will remove the glare from light reflected from objects when the lines 58 are oriented horizontally. This occurs as a result of light waves striking the reflecting object being unable to pass through the finely separated lines 58.

If polarizer 57 is rotated such that lines 58 are not substantially horizontal, then the glare will return as the light waves will be able to pass through the polarizer 57. The lines 58 will be invisible in either event to the observer. Rotating polarizer 57 will thus result in a reflecting object flashing in proportion to the speed of rotation. For visual determinations of the flash, revolutions of about 2 to 4 per second are desired. If the object being observed is of a type that is man-made, having a smooth appearance and having both vertical and horizontal surfaces, then flashes will occur both when the polarizer 57 has its lines 58 oriented horizontally and when oriented vertically. At 2 to 4 revolutions per second, approximately 7 flashes per second would be observed to the human eye. This is a flash rate that will naturally draw the eye/mind system's attention.

The rotation means for rotating polarizer 57 includes a set of gear teeth 59 formed on the circular perimeter of polarizer 57. Gear teeth 59 may be formed integrally or may be formed on a ring that is secured or pressed fitted to the perimeter of polarizer 57. A drive gear 61 has teeth which will engage teeth 59. A DC electrical motor 63 will drive drive gear 61. A battery or other power source (not shown) supplies power for motor 63. A switch (not shown) enables the observer to selectively turn motor 63 on and off.

Video camera 55 is of a conventional type. Objects viewed by video camera 55 are converted into electrical signals which are displayed electronically. Video camera 55 will produce flashing or pulsing images reflected from man-made objects having smooth non-light conducting surfaces. Video camera 55 has a lens array which defines an image path for light received. A conventional signal processor in video camera 55 will produce analog electrical signals proportional to the objects viewed. In a conventional video camera system, these signals may be recorded on video tape or film. Also, the signals may pass to a television monitor or display for viewing.

In this invention, the electrical signals from video camera 55 first pass through a high pass cut-on electronic filter 64 before being displayed on monitor 67. Filter 64 is of a high pass type which will pass signals above the cut-on frequency and block, filter, or delete those below, all which are referred to herein as "filter". This cut-on or selected frequency is selected to be high enough to eliminate much of the background objects which reflect light that is not affected by the rotating polarizer 57. This frequency is much higher than the frequency of rotation of polarizer 57. natural objects. Filter 64 is preferably variable so that its cut-on or pass frequency can be varied. The user will watch monitor 67 while rotating polarizer 57. Light reflected from man-made objects will appear to flash as the polarizer 57 rotates. Most natural objects in the background will not flash, because the reflected light from natural surfaces usually does not produce a strong polarizing contrast. These objects include most natural objects, such as trees, foliage, earth and the like, due to the texture of these surfaces, and some man-made objects such as camouflage. The user adjusts filter 64 until much of the background is eliminated, but the flashing objects due to rotating polarizer 57 remain visible.

In one test using a conventional video camera and an adjustable filter 64, the cut-on frequency was determined to be effective if set in the range from 100 KHZ (kilohertz) to two MHZ (megahertz). While in this range, flashing objects due to rotating polarizer 57 were enhanced and background objects such as sky, foliage and concrete were reduced and roughened. The elimination is due to both roughness and the fact that man-made nonconductors have a large polarization differential.

Signals from the high pass filter 64 may proceed directly to monitor 67. Additionally, the signals from high pass filter 64 may be further processed by a discriminator circuit 65 before being displayed on monitor 67. Discriminator circuit 65 will selectively delete objects which flash only when polarizer 57 is in a horizontal orientation or in a vertical orientation. Consequently, discriminator circuit 65 will not pass signals representing sky or lakes to monitor 67. Only an object having both generally horizontal and vertical surfaces that reflect light which polarizes will be displayed by monitor 67.

Figure 3:
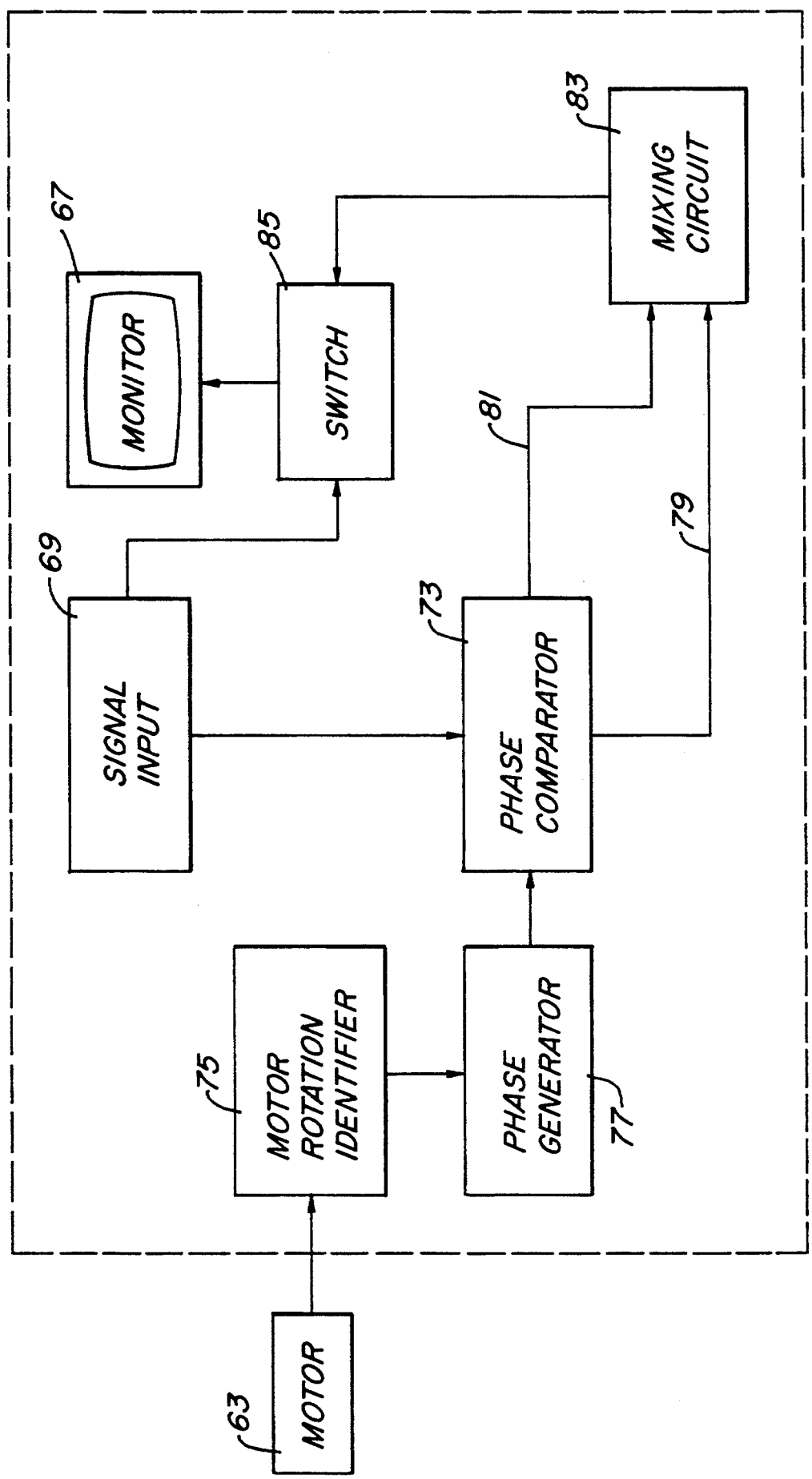
FIG. 3 is a more detailed block diagram of the discriminator circuit utilized with the video camera of FIG. 1.

FIG. 3 represents more details of the discriminator circuit 65. The circuit 65 will include a signal input 69 which receives electrical signals from video camera 55 based on scanning by camera 55 and preferably after passing through high pass filter 64. Signals from signal input 69 pass to a phase comparator 73. At the same time, a motor rotation identifier 75 will be monitoring accurately the speed of rotation of motor 63. Motor rotation identifier 75 leads to a phase generator 77. Phase generator 77 and motor rotation identifier 75 will continuously and precisely determine not only the speed of rotation, but also the instantaneous orientation of the lines contained on the polarizer 57. Phase generator 77 will generate a signal that indicates when the lines of polarizer 57 are in a horizontal position. A different signal will be generated indicating when phase generator 77 has its lines oriented vertically. These alternating signals are 90 degrees out of phase with each other and are applied to the phase comparator 73.

The phase comparator 73 will compare the alternating signal from the phase generator 77 to determine if a lesser intensity signal, or polarization, occurred simultaneously when the polarizer 57 was horizontal. Similarly, phase comparator 73 will determine if a lesser intensity signal or polarization occurred when the polarizer 57 was vertical. If polarization occurred when polarizer 57 was vertical, the signal passes from phase comparator 73, as indicated by output signal 81. If polarization occurred when polarizer 57 was horizontal, a signal will pass from phase comparator 73, as indicated by output signal 79.

The vertical component signals 81 and the horizontal component signals 79 are applied to a mixing circuit 83. The mixing circuit 83 inverts one of the signals 79, 81 and adds the two. If a vertical component signal 81 immediately followed a horizontal component signal 79, then mixing circuit 83 will forward the combined signal through a switch 85 to monitor 67. Monitor 67 will visually display an object which has provided the vertical and horizontal component signals 81, 79. On the other hand, if a horizontal component 79 does not immediately follow a vertical component 81 in time sequence corresponding to the rotation of motor 63, then mixing circuit 83 will not provide a signal to monitor 67. The added signals would not meet a threshold in mixing circuit 83. This condition indicates that the object was flashing only when polarizer 57 was either vertical or horizontal, not in both positions. This indicates that the object is not a man-made object having vertical and horizontal surfaces. Therefore, it is excluded from monitor 67.

Switch 85 is manually accessible. It allows the operator to selectively pass the signals from frequency filter 64 (FIG. 1) directly to monitor 67. The operator in this manner could visually determine if an object is of interest, rather than utilizing the circuitry which excludes objects not having horizontal and vertical components.

Figure 4:
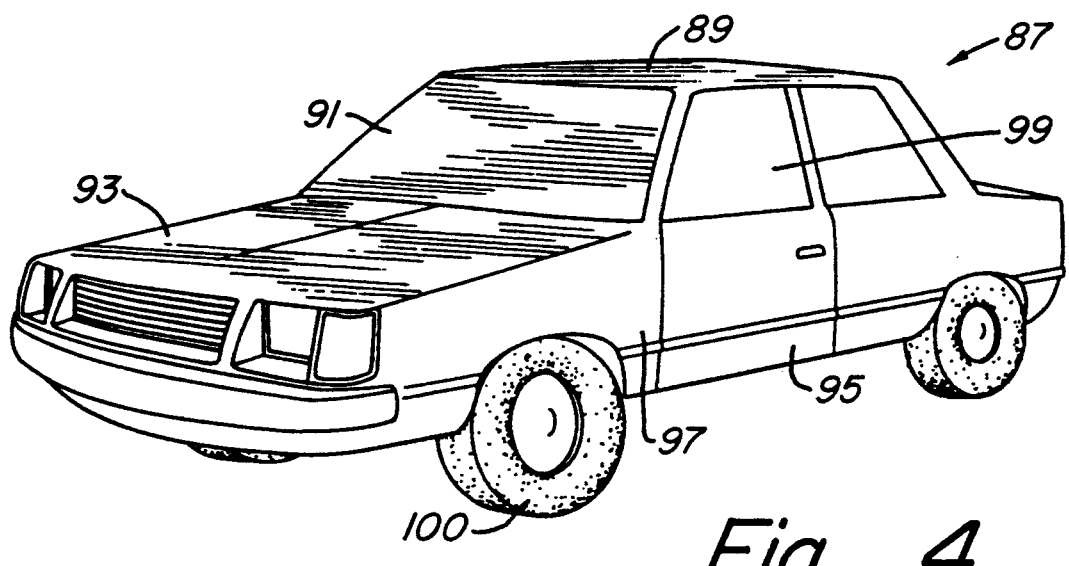
FIG. 4 is a perspective view of a vehicle illustrating light being polarized by a horizontally-oriented polarizer.
Figure 5:
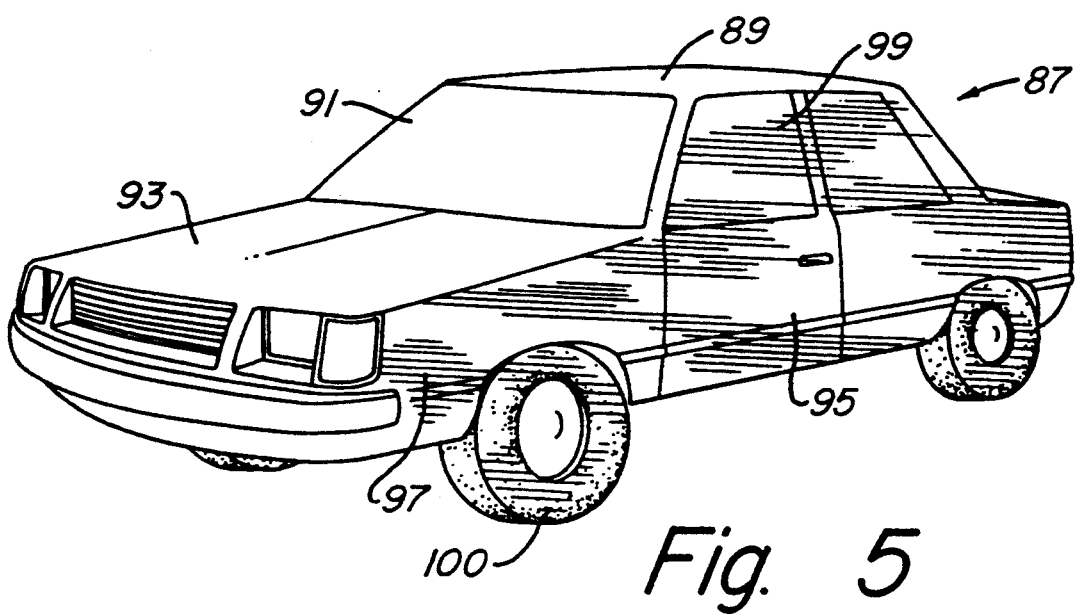
FIG. 5 illustrates the vehicle of FIG. 4 with the light being polarized when the polarizer is in a vertical position.
Figure 6:
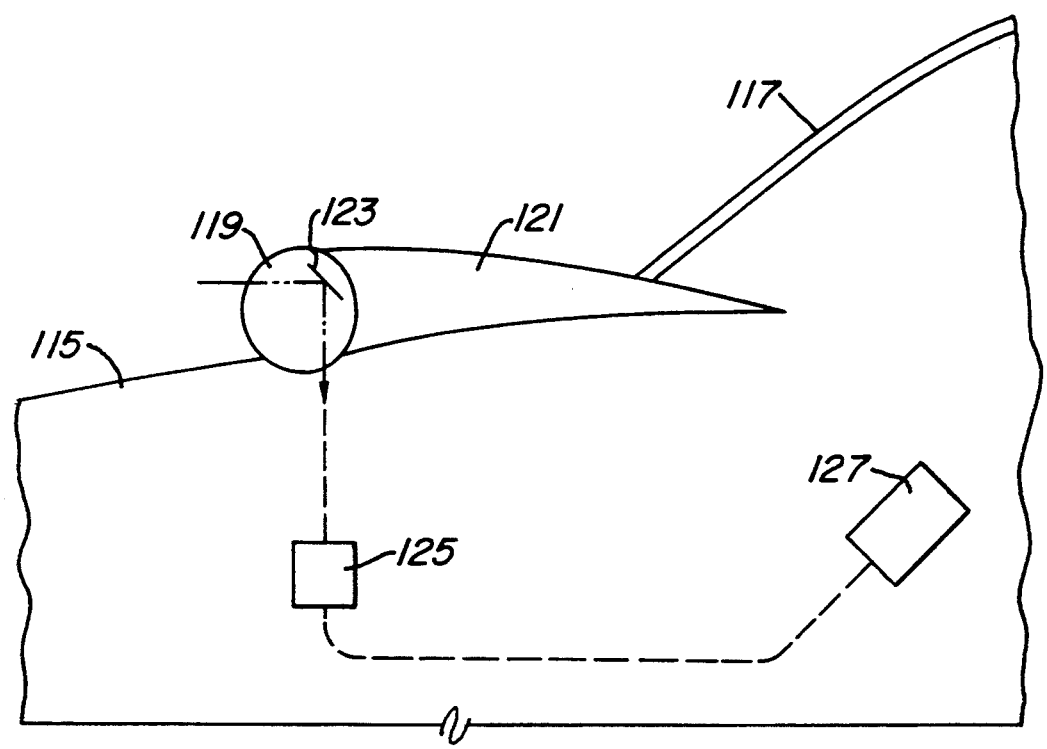
FIG. 6 is a schematic side view of a portion of an airplane having a detection system constructed in accordance with this invention.

FIGS. 4 and 5 illustrate the types of horizontal and vertical components that may be observed and detected with the circuitry of FIG. 3. Vehicle 87 has a roof 89 that will be horizontally oriented if on flat terrain. Windshield 91 inclines, thus possibly providing both vertical and horizontal reflections, but normally will reflect more in a horizontal mode as does roof 89. Hood 93 is typically in approximately the same plane as roof 89. Doors 95, fenders 97, side windows 99 and tires 100 will normally be nearly vertical. The darkened lines in FIGS. 4 and 5 show the differences in polarizing contrast that occurs due to rotation of polarizer 57.

In FIG. 4, the vertical surfaces from door 95, fender 97, side windows 99 and tires 100 are reflecting light which is not being polarized. This indicates that the polarizer 57 is oriented other than with its lines vertical. Conversely, the flat horizontal surfaces of roof 89, windshield 91 and hood 93 reflect light which is being Conversely, the flat horizontal surfaces of roof 89, windshield 91 and hood 93 reflect light which is being polarized. These reflections are occurring in the horizontal plane, confirming that polarizer 57 is oriented with its lines in a horizontal position. In FIG. 5, the reverse occurs. Roof 89, windshield 91 and hood 93 reflect light that is not polarized, while door 95, fender 97, side windows 99 and tires 100 reflect light that is polarized. This indicates that the polarizer 57 has rotated to a vertical position in which its lines are oriented vertically, 90 degrees from the position observed in FIG. 4.

In operation, motor 63 rotates polarizer 57. Assuming that video camera 55 is pointed at vehicle 87 of FIGS. 4 and 5, flashes will occur. The video camera 55 will produce an electrical signal which represents not only the flashes from vehicle 87, but also all of the background being observed, such as the surrounding trees, hills and other terrain. High pass frequency filter 64 will pass only signals above a selected frequency, passing signals which are cycling in intensity, indicating that the flashing is due to rotation of polarizer 57. As no flashing will occur, or very little, due to the natural terrain, much of the signals representing the terrain will be blocked by filter 64. The signals representing most of the vehicle 87 will pass through frequency filter 64. If switch 85 is in one position, flashing portions of the vehicle 87 will then be displayed on monitor 67.

At the same time, phase comparator 73 will compare the flashing being observed to an alternating signal produced by phase generator 77. Phase comparator 73 will determine if polarizing occurs when the polarizer 57 is oriented with its lines vertical. If so, vertical component 81 then passes to mixing circuit 83. This occurs as illustrated in FIG. 5, with the door 95, fenders 97, side windows 99 and tires 100 producing reflected light that is polarized due to the vertical orientation of polarizer 57. The reflection from roof 89, generator 77 indicates that the polarizer 57 is oriented horizontally. If so, horizontal component 79 passes to mixing circuit 83. This is the instance that occurs in FIG. 4. In that figure, light reflected from roof 89, windshield 91 and hood 93 is polarized due to the horizontal orientation of polarizer 57. Now, the reflection from door 95, fenders 97, side windows 99 and tires 100 is not polarized.

Mixing circuit 83 will pass the signal on to monitor 67 if switch 85 is in the proper position and if it receives both components 79, 81 in alternating sequence. If the object was a body of water, then no signal would pass from mixing circuit 83, because it would not produce reflected light that would cause a flash to occur both when the polarizer 57 is oriented horizontally and oriented vertically.

FIG. 9 illustrates a portion of a fuselage 115 of an airplane. Fuselage 115 has a canopy 117. A transplant ball 119 rotatably mounts to fuselage 115, in front of and to one side of canopy 117. Ball 119 can be rotated for alignment and contains a focusing lens system which focuses light onto a mirror 123. Mirror 123 reflects light down to a detection system 125 inside fuselage 115. Detection system 125 provides a signal over wires to a monitor 127 located in the cockpit. In the prior art, a similar arrangement is used for conventional infrared surveillance. Detection system 125 comprises video camera 55, high pass filter 64 and discriminator circuit 65 (FIG. 1).

The invention has significant advantages. It allows military target detection through camouflage and light foliage. The polarizing lens and associated rotating drive system and circuitry can be added without significant expense to existing video cameras. The system can be employed in helicopters to prevent pilots from colliding with power cables.

While the invention has been shown in only one of its forms, it should be apparent to those skilled in the art that it is not so limited but is susceptible to various changes without departing from the scope of the invention.

I claim:

1. An apparatus for detecting selected objects, comprising in combination:

video camera means having an image path for receiving reflected light from objects at which the video camera means is pointed and for providing electrical signals for electronically displaying the objects viewed;

a polarizer mounted to the video camera means in the image path for for alternately polarizing light received from objects and transmitted through the video camera means to produce alternating contrasts in intensity in rapid sequence of the light being polarized; and frequency filter means for filtering electrical signals produced by the video camera means below a selected frequency which is selected to substantially reduce the display of background objects viewed which reflect light that does not differ when passing through the rotating polarizer, and for passing electrical signals produced by the video camera means above the selected frequency.

2. The apparatus according to claim 1 wherein the selected frequency is in the range between 100 KHZ and two MHZ.

3. The apparatus according to claim 1 wherein the polarizer means alternately polarizes light at a frequency that is much less than the selected frequency of the frequency filter means.

4. The apparatus according to claim 1 wherein the video camera means includes a video signal processor which provides the electrical signals and a video monitor which receives the electrical signals, and wherein the frequency filter means locates between the video signal processor and the video monitor.

5. The apparatus according to claim 1 wherein the polarizer means alternately horizontally and vertically polarizes light and wherein the apparatus further comprises a discriminating means, which comprises:

phase comparator means for determining if the polarizer means has horizontally polarized light reflected from the object and has vertically polarized light reflected from the object, and for producing a horizontal component signal and a vertical component signal corresponding thereto if both horizontal and vertical polarization did occur; and means receiving each of the signals from the phase comparator means for determining if a horizontal component signal is being received that alternates in time with a vertical component signal being received, and if so, passing the horizontal and vertical component signals to a monitor for viewing.

6. The apparatus according to claim 1 further comprising means for mounting the apparatus to a fuselage of an airplane.

7. The apparatus according to claim 1 wherein the polarizer means alternately horizontally and vertically polarizes light, and wherein the apparatus further comprises:

means for determining if a first condition exists wherein a portion of the object being observed reflects more intense light when the polarizer means is horizontally polarizing light than when vertically polarizing light;

means for determining if a second condition exists in which a portion of the object being observed reflects more intense light when the polarizer means is horizontally polarizing light than when vertically polarizing light; and means for providing an indication to a viewer if both of said conditions exist, indicating an object which has generally horizontal and vertical surfaces, each of which reflects light which will polarize.

8. An apparatus for detecting selected objects, comprising in combination:

video camera means having an image path for receiving reflected light from objects at which the video camera means is pointed, a video signal processor for providing electrical signals corresponding to the objects viewed, and a monitor which receives the electrical signals for electronically displaying the image;

a polarizer mounted to the video camera means in the image path for rotation about an axis of rotation;

rotational means for rotating the polarizer about the axis of rotation to produce alternating contrasts in intensity of the light being polarized; and frequency filter means located between the video signal processor and the monitor for filtering electrical signals produced by the video signal processor below a selected frequency, the selected frequency being in the range from 100 KHZ to two MHZ.

9. The apparatus according to claim 8 wherein the rotational means comprises:

a motor; and drive means between the motor and the polarizer for rotating the polarizer.

10. The apparatus according to claim 8 wherein the polarizer has a plurality of spaced-apart parallel lines and wherein the apparatus further comprises a discriminating means, which comprises:

phase comparator means for determining if the polarizer polarized light reflected from the object when the lines are in a horizontal position and when in a vertical position, and for producing a horizontal component signal and a vertical component signal corresponding thereto if polarization did occur during both positions; and means receiving each of the signals from the phase comparator means for determining if a horizontal component signal is being received that alternates in time with a vertical component signal being received, and if so, passing the horizontal and vertical component signals to the monitor for viewing.

11. The apparatus according to claim 8 further comprising means for mounting the apparatus to a fuselage of an airplane.

12. The apparatus according to claim 8 wherein the rotational means rotates the polarizer through horizontal and vertical positions, and wherein the apparatus further comprises:

means for determining if a first condition exists wherein a portion of the object being observed reflects more intense light when the polarizer is in the horizontal position than when in the vertical position;

means for determining if a second condition exists in which a portion of the object being observed reflects more intense light when the polarizer is in the vertical position than when in the horizontal position; and means for providing the signal to the video monitor if both of said conditions exist, indicating an object which has generally horizontal and vertical surfaces, each of which reflects light which will polarize, and for preventing the signal from passing to the video monitor if both of said conditions do not exist.

13. A method for searching for selected objects, comprising:

providing a video camera having an image path for receiving reflected light from objects at which the video camera is pointed;

providing a polarizer;

mounting the polarizer in alignment with the image path;

passing light reflected from the objects through the polarizer and determining if any of the light will horizontally polarize, creating a first image, and if any of the light will vertically polarize, creating a second image, and rapidly alternating the first and second images so as to create alternating contrasts in intensity of the light being polarized;

providing electrical signals from the video camera means in response to the objects viewed; and filtering the electrical signals produced by the video camera below a selected frequency which is selected to substantially reduce the display of background objects viewed which reflect light that does not differ when passing through the rotating polarizer, and passing electrical signals produced by the video camera above the selected frequency.

14. The apparatus according to claim 13 wherein the selected frequency is in the range between 100 KHZ and two MHZ.

15. The method according to claim 13 further comprising:

determining if a first condition exists wherein a portion of an object reflects brighter light when the polarizer is horizontally polarizing light than when vertically polarizing light;

determining if a second condition exists wherein a portion of an object reflects brighter light when the polarizer is vertically polarizing light than when horizontally polarizing light; and providing an indication to a viewer if both of said conditions exist, indicating an object which has a surface that is generally horizontal, and another surface that is generally vertical, both of the surfaces being capable of reflecting light that may be polarized.

16. A method for searching for selected objects, comprising:

providing a video camera having an image path for receiving reflected light from objects at which the video camera is pointed, a video signal processor for providing electrical signals in response to the objects viewed, and a monitor for displaying the object in response to the electrical signals received from the video signal processor;

providing a polarizer;

mounting the polarizer about an axis of rotation in alignment with the image path;

rotating the polarizer about the axis of rotation, providing alternating contrasts in intensity of the light being polarized;

providing electrical signals from the video signal processor in response to the objects viewed; and filtering the electrical signals produced by the video signal processor below a selected frequency which selected to be in the range from 100 KHZ to two MHZ.

17. The method according to claim 16 wherein the polarizer passes through horizontal and vertical positions as it rotates and wherein the method further comprises:

determining if a first condition exists wherein a portion of an object reflects brighter light when the polarizer is in a horizontal position than when in a vertical position;

determining if a second condition exists wherein a portion of an object reflects brighter light when the polarizer is in the vertical position than when in the horizontal position; and passing the signal from the video signal processor to the monitor if both of said conditions exist, indicating an object which has a surface that is generally horizontal, and another surface that is generally vertical, both of the surfaces being capable of reflecting light that may be polarized, and blocking signals from the video signal processor to the monitor if both of said conditions exist.

* * * * *